US00PP16138P3

(12) United States Plant Patent

Miyazaki et al.

(10) Patent No.: US PP16,138 P3
(45) Date of Patent: Dec. 6, 2005

(54) **BOTANICAL/COMMERCIAL CLASSIFICATION *VIOLA CORNUTA/VIOLA* PLANT VARIETAL DENOMINATION CV. 'SUNVIOKI'**

(50) Latin Name: *Viola cornuta*
Varietal Denomination: Sunvioki

(75) Inventors: Kiyoshi Miyazaki, Hikone (JP); Naoto Takamura, Omihachiman (JP); Yukihiro Ikeda, Akashi (JP)

(73) Assignee: Suntory Flowers Limited, Tokyo (JP)

( * ) Notice: Subject to any disclaimer, the term of this patent is extended or adjusted under 35 U.S.C. 154(b) by 137 days.

(21) Appl. No.: 10/611,807

(22) Filed: Jun. 30, 2003

(65) Prior Publication Data

US 2004/0143877 P1 Jul. 22, 2004

(30) Foreign Application Priority Data

Dec. 26, 2002 (JP) ..... 15366

(51) Int. Cl.[7] ..... A01H 5/00
(52) U.S. Cl. ..... Plt./323

(58) Field of Search ..... Plt./323

(56) References Cited

PUBLICATIONS

Catalogue for Profit Organization, 2002 Fall–2003 Spring, No. 78, 4 pages, Published by Sakata Seed Co., Japan, May 2002 with English explanation.
Catalogue for Profit Organization, 2002–2003, 5 pages, Published by Takii Seed Co., Japan, Apr. 2002 with English explanation.
2004 Product Portfolio, pp. 34, published by S & G Flowers (3 pgs).

*Primary Examiner*—Kent Bell
(74) *Attorney, Agent, or Firm*—Christie, Parker and Hale, LLP

(57) ABSTRACT

Disclosed herein is new *Viola cornuta* plant named 'Sunvioki', which is a vegetative propagated variety, developed by specific hybridization between '9V-39a' and 'Alpine Sun'. 'Sunvioki' has a spreading habit with very long stem. The plant height is low. The branching is abundant. Flowers are vertically oblong and very small. The color of flower is brilliant greenish yellow with vivid yellow eye. The plant has a high resistance to cold, pests and diseases.

2 Drawing Sheets

Botanical/commercial classification: *Viola cornuta/Viola* Plant.
Varietal denomination: cv. 'Sunvioki'.

BACKGROUND OF THE VARIETY

The genus of *Viola* is included in the family Violaceae, and has about 500 species of annuals, biennials, evergreen, and semi-evergreen and deciduous perennials found in varied habitats in temperature regions worldwide.

Each flower has 5 petals: a spurred lower petal, 2 lateral petals and 2 upward-facing upper petals.

Many cultivars within the genus are informally referred to as garden pansies. *Violas* are all derived from the complex hybridization of *V.tricolour, V.lutea, V.cornuta*, and other species.

*Viola cornuta* has played an important role in the development of garden *violas* and violettas as a result of cross breeding with the garden pansy, *V. wittorockiana.*

*Viola cornuta* is stem prostrate. Leaves are narrow to broad ovate, base cordate to truncate, margin deeply segmented.

The female parent used in the crossing for obtaining 'Sunvioki' was '9V-39a' (not patented in the United States.

The pollen parent used in the crossing for obtaining of 'Sunvioki' is a commercial cultivar, 'Alpine Sun'.

BREEDING PROCESS

Crossing between '9V-39a' as female parent and 'Alpine Sun' as male parent was conducted in Shiga-ken, Japan, in April 2000. In May, seeds were obtained from the crossing. In August, three seedlings were selected in view of having highly spreading habit with yellow petals, and were propagated by cutting. A trial was carried out for those seedlings by flower potting and bedding from October 2001. One variety was selected in view of having long blooming time. The botanical characteristics of that plant were then examined, using similar varieties 'Alpine Spring' and 'Violetto Lune' for comparison. As a result, it was concluded that this *Viola cornuta* plant is distinguishable from any other variety, whose existence is known to us, and uniform and stable in its characteristics. Thenew variety of *Viola cornuta* plant was named 'Sunvioki'.

This new and distinct variety of *Viola cornuta* plant, 'Sunvioki', was asexually reproduced by tissue culture and the homogeneity and stability thereof were confirmed. The new variety reproduces true to type in successive generations of asexual reproduction.

*Viola cornuta* plants, '9V-39a' and 'Alpine Sun' are presently maintained at Shiga-ken, Japan.

DESCRIPTION

In the following description, the color-coding is in accordance with the Horticultural Colour Chart of The Royal Horticultural Society, London, England (R.H.S.).

The botanical characteristics of the female parent plant '9V-39a' used in the crossing of 'Sunvioki' are as follows.

Plant:
*Stemmed or non-stemmed.*—Stemmed.
*Growth habit.*—Spreading.
*Height.*—Approximately 9 cm.
*Plant cover.*—Approximately 49 cm.
Stem:
*Length.*—Approximately 36 cm.
*Branching.*—Much.
*Pubescence.*—Present.
Leaf:
*Overall form.*—Long oblong.
*Apex form.*—Acute.
*Base form.*—Acute.
*Serrated, lobed or not.*—Serrated or lobed.
*Margin.*—Serrated or slightly lobed.
*Length.*—Approximately 1.9 cm.
*Width.*—Approximately 1.2 cm.
*Color of upper surface.*—Grayish olive green (near R.H.S. 137A).
*Color of under surface.*—Moderate yellow green (near R.H.S. 137C).
*Variegation.*—Absent.
*Leaf luster.*—Lustrous.
*Vein.*—Distinct.
*Petiole length.*—Approximately 1.4 cm.
*Stipule length.*—Approximately 1.8 cm.
Flower:
*Peduncle length.*—Approximately 7.5 cm.
*Peduncle thickness.*—Thin.
*Peduncle color.*—Strong yellow green (near R.H.S. 144B).
*Flower form.*—Vertically oblong.
*Flowering direction.*—Upward.
*Longitudinal diameter.*—Approximately 3.2 cm.
*Horizontal diameter.*—Approximately 3.0 cm.
*Ruffle of petal margin.*—Weakly ruffled.
*Petal curving.*—Very weak.
*Petal number.*—Single.
*Flower color.*—Single-colored.
*Upper petal.*—Form — Round. Size — Approximately 1.6×1.6 cm. Petal color — Single-colored. Ground color — Pale yellow green (near R.H.S. 157A). Blotch — Absent.
*Side petal.*—Form — Ovate. Size — Approximately 1.3×1.5 cm. Petal color — Single-colored. Ground color — Pale yellow green (near R.H.S. 157A). Blotch — Absent.
*Lower petal.*—Form — Cordate. Size — Approximately 1.9×1.9 cm. Petal color — Single-colored. Ground color — Pale yellow green (near R.H.S. 157A). Blotch — Absent. Eye color — Vivid reddish yellow (near R.H.S. 14A). Eye size — Medium.
*Thickness of petal.*—Medium.
*Spur length.*—Longer than the sepal appendage.
*Sepal.*—Short.
*Number of flowers.*—Many.
Seed:
*Color.*—Deep brown.
Physical property:
*Flowering time.*—Late.
*Fragrance.*—Faint or weak.
*Resistance.*—Rain — Strong. Cold — Strong. Heat — Medium. Disease — Strong. Pest — Strong.

The botanical characteristics of the male parent plant 'Alpine Sun' used in the crossing of 'Sunvioki' are as follows.

Plant:
*Stemmed or non-stemmed.*—Stemmed.
*Growth habit.*—Spreading.
*Height.*—Approximately 8 cm.
*Plant cover.*—Approximately 35 cm.
Stem:
*Length.*—Approximately 25 cm.
*Branching.*—Much.
*Pubescence.*—Present.
Leaf:
*Overal form.*—Long oblong.
*Apex form.*—Obtuse.
*Base form.*—Acute.
*Serrated, lobed or not.*—Serrated or lobed.
*Margin.*—Serrated or slightly lobed.
*Length.*—Approximately 2.1 cm.
*Width.*—Approximately 1.0 cm.
*Color of upper surface.*—Grayish olive green (near R.H.S. 137A).
*Color of under surface.*—Moderate yellow green (near R.H.S. 137C).
*Variegation.*—Absent.
*Leaf luster.*—Matte.
*Vein.*—Apparent.
*Petiole length.*—Approximately 2.2 cm.
*Stipule length.*—Approximately 2.1 cm.
Flower:
*Peduncle length.*—Approximately 8.0 cm.
*Peduncle thickness.*—Thin.
*Peduncle color.*—Strong yellow green (near R.H.S. 144B).
*Flower form.*—Vertically oblong.
*Flowering direction.*—Upward.
*Longitudinal diameter.*—Approximately 3.3 cm.
*Horizontal diameter.*—Approximately 2.5 cm.
*Ruffle of petal margin.*—Flat.
*Petal curving.*—Weak.
*Petal number.*—Single.
*Flower color.*—Single-colored.
*Upper petal.*—Form — Round. Size — Approximately 1.1×1.0 cm. Petal color — Self-colored. Ground color — Vivid yellow (near R.H.S. 9B). Blotch — Absent.
*Side petal.*—Form — Ovate. Size — Approximately 1.2×1.0 cm. Petal color — Single-colored. Ground color — Vivid yellow (near R.H.S. 9B). Blotch — Absent.
*Lower petal.*—Form — Cordate. Size — Approximately 1.4×1.3 cm. Petal color — Single-colored. Ground color — Vivid yellow (near R.H.S. 9A). Blotch — Absent. Eye color — Vivid yellow (near R.H.S. 13A). Eye size — Small.
*Thickness of petal.*—Thin.
*Spur length.*—Longer than the sepal appendage.
*Sepal.*—Short.
*Number of flowers.*—Many.
Seed:
*Color.*—Deep brown.
Physical property;
*Flowering time.*—Late.
*Fragrance.*—Absent.

*Resistance.*—Rain — Medium. Cold — Strong. Heat — Medium. Disease — Strong. Pest — Strong.

The botanical characteristics of the similar variety 'Alpine Spring' used for examination as a comparison are as follows.

Plant:
*Stemmed or non-stemmed.*—Stemmed.
*Growth habit.*—Spreading.
*Height.*—Approximately 8 cm.
*Plant cover.*—Approximately 35 cm.
Stem:
*Length.*—Approximately 25 cm.
*Branching.*—Much.
*Pubescence.*—Present.
Leaf:
*Overal form.*—Long oblong.
*Apex form.*—Obtuse.
*Base form.*—Acute.
*Serrated, lobed or not.*—Serrated or lobed.
*Margin.*—Serrated or slightly lobed.
*Length.*—Approximately 2.1 cm.
*Width.*—Approximately 1.0 cm.
*Color of upper surface.*—Grayish olive green (near R.H.S. 137A).
*Color of under surface.*—Moderate yellow green (near R.H.S. 137C).
*Variegation.*—Absent.
*Leaf luster.*—Matte.
*Vein.*—Apparent.
*Petiole length.*—Approximately 2.2 cm.
*Stipule length.*—Approximately 2.1 cm.
Flower:
*Peduncle length.*—Approximately 8.0 cm.
*Peduncle thickness.*—Thin.
*Peduncle color.*—Strong yellow green (near R.H.S. 144B).
*Flower form.*—Vertically oblong.
*Flowering direction.*—Upward.
*Longitudinal diameter.*—Approximately 3.3 cm.
*Horizontal diameter.*—Approximately 2.5 cm.
*Ruffle of petal margin.*—Flat.
*Petal curving.*—Weak.
*Petal number.*—Single.
*Flower color.*—Single-colored.
*Upper petal.*—Form — Round. Size — Approximately 1.1×1.0 cm. Petal color — Single-colored. Ground color — Brilliant yellow green (near R.H.S. 2B). Blotch — Absent.
*Side petal.*—Form — Ovate. Size — Approximately 1.2×1.0 cm. Petal color — Single-colored. Ground color — Vivid yellow (near R.H.S. 9B). Blotch — Absent. Vein color — Dark reddish purple (near R.H.S. 79A).
*Lower petal.*—Form — Cordate. Size — Approximately 1.4×1.3 cm. Petal color — Single-colored. Ground color — Vivid yellow (near R.H.S. 9A). Blotch — Absent. Vein color — Dark reddish purple (near R.H.S. 79A). Eye color — Vivid yellow (near R.H.S. 13A). Eye size — Small.
*Thickness of petal.*—Thin.
*Spur length.*—Longer than the sepal appendage.
*Sepal.*—Short.
*Number of flowers.*—Many.
Seed:
*Color.*—Deep brown.
Physical property:
*Flowering time.*—Late.
*Fragrance.*—Absent.
*Resistance.*—Rain — Medium. Cold — Strong. Heat — Medium. Disease — Strong. Pest — Strong.

The botanical characteristics of the similar variety 'Violetto Lune' used for examination as a comparison are as follows.

Plant:
*Stemmed or non-stemmed.*—Stemmed.
*Growth habit.*—Spreading.
*Height.*—Approximately 6 cm.
*Plant cover.*—Approximately 40 cm.
Stem:
*Length.*—Approximately 26 cm.
*Branching.*—Much.
*Pubescence.*—Present.
Leaf:
*Overal form.*—Long oblong.
*Apex form.*—Obtuse.
*Base form.*—Obtuse.
*Serrated, lobed or not.*—Serrated or lobed.
*Margin.*—Serrated or slightly lobed.
*Length.*—Approximately 2.2 cm.
*Width.*—Approximately 1.6 cm.
*Color of upper surface.*—Grayish olive green (near R.H.S. 137B).
*Color of under surface.*—Moderate yellow green (near R.H.S. 137C).
*Variegation.*—Absent.
*Leaf luster.*—Matte.
*Vein.*—Apparent.
*Petiole length.*—Approximately 1.3 cm.
*Stipule length.*—Approximately 2.0 cm.
Flower:
*Peduncle length.*—Approximately 9.0 cm.
*Peduncle thickness.*—Thin.
*Peduncle color.*—Strong yellow green (near R.H.S. 144B).
*Flower form.*—Vertically oblong.
*Flowering direction.*—Horizontal.
*Longitudinal diameter.*—Approximately 3.4 cm.
*Horizontal diameter.*—Approximately 2.9 cm.
*Ruffle of petal margin.*—Flat.
*Petal curving.*—Weak.
*Petal number.*—Single.
*Flower color.*—Single-colored.
*Upper petal.*—Form — Round. Size — Approximately 1.9×1.9 cm. Petal color — Single-colored. Ground color — Vivid yellow (near R.H.S. 9A). Blotch — Absent.
*Side petal.*—Form — Round. Size — Approximately 1.2×1.1 cm. Petal color — Single-colored. Ground color — Vivid yellow (near R.H.S. 9A). Blotch — Absent.
*Lower petal.*—Form — Cordate. Size — Approximately 1.8×1.1 cm. Petal color — Single-colored. Ground color — Vivid yellow (near R.H.S. 12A). Blotch — Absent. Eye color — Vivid yellow (near R.H.S. 13A). Eye size — Small.
*Thickness of petal.*—Thin.
*Spur length.*—Longer than the sepal appendage.
*Sepal.*—Short.
*Number of flowers.*—Many.

Seed:
*Color.*—Deep brown.
Physical property:
*Flowering time.*—Late.
*Fragrance.*—Absent.
*Resistance.*—Rain — Medium. Cold — Strong. Heat — Medium. Disease — Strong. Pest — Strong.

SUMMARY OF THE NEW VARIETY

The new variety of *viola* plant named 'Sunvioki', which is a vegetative propagated variety, has a spreading plant habit with very long epigeal stem. The plant height is low and the branching is abundant. The flowers of the new variety are vertically oblonged and very small, and the color of flower is brilliant greenish yellow with vivid yellow eye. The new variety has a high resistance to cold, pests and diseases.

DESCRIPTION OF THE VARIETY

Figure 1:
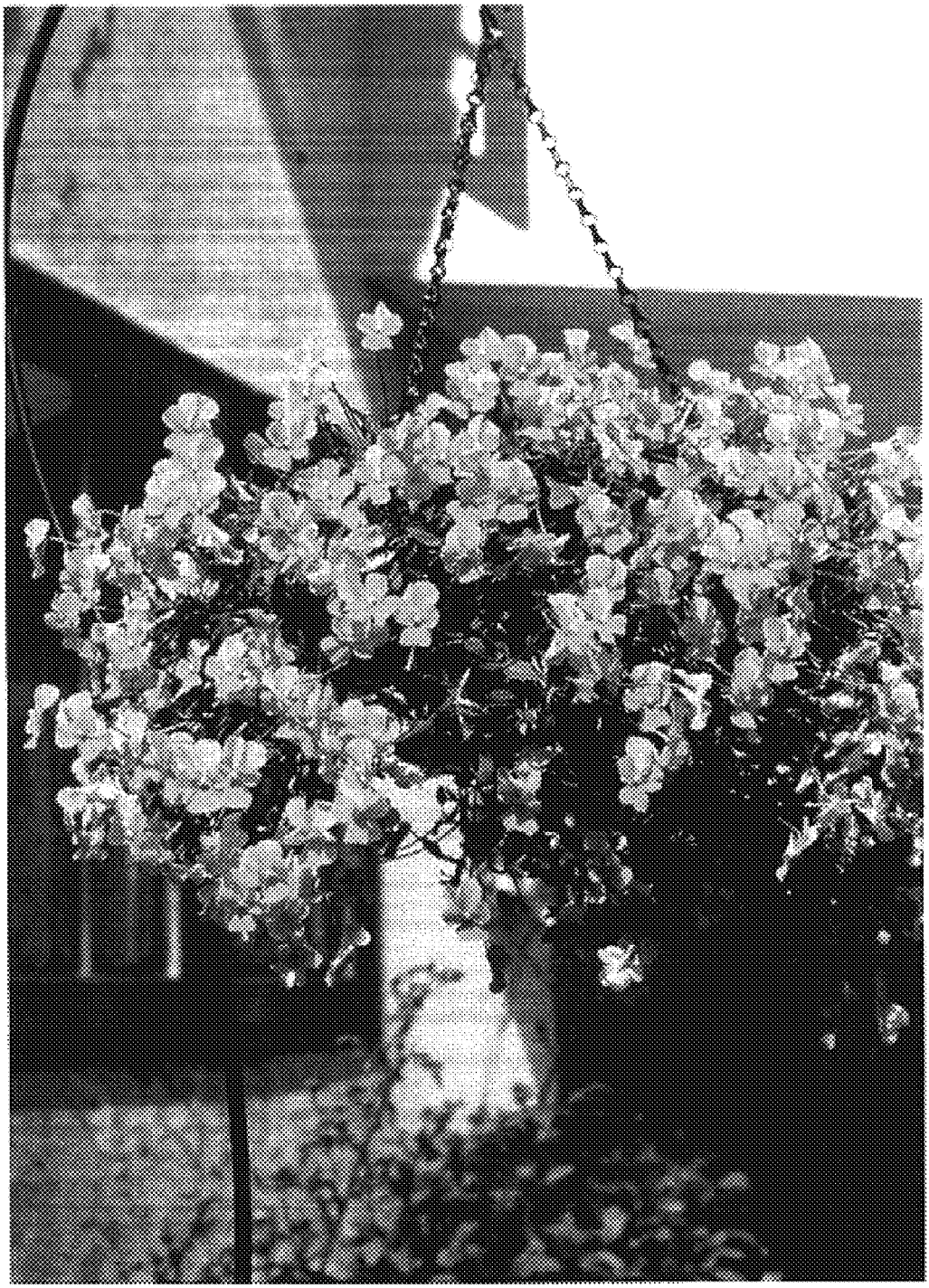
FIG. 1 is a photograph giving a partial view of the new variety of *Viola cornuta* plant 'Sunvioki' planted in pots.
Figure 2:
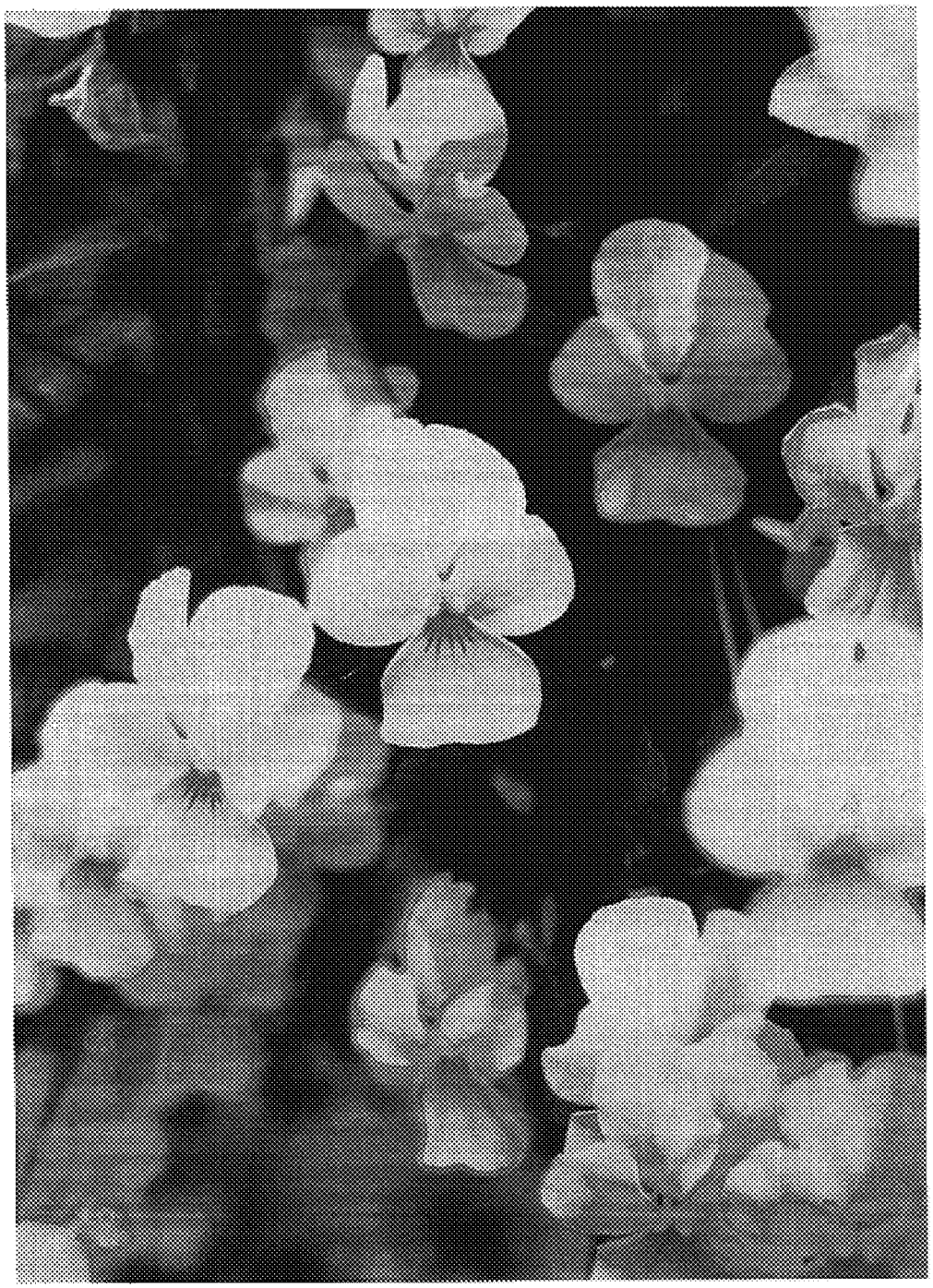
FIG. 2 is a photograph of flowers of the new variety of *Viola cornuta* plant 'Sunvioki'.

The botanical characteristics of this new and distinct variety of *Viola cornuta* plant named 'Sunvioki' are as follows. The plant was observed at Yokaich-shi, Shiga-ken, Japan. The plant was approximately seven months old and was grown in a 30 cm diameter container.

Plant:
*Stemmed or non-stemmed.*—Stemmed.
*Growth habit.*—Spreading.
*Height.*—Approximately 8 cm.
*Plant cover.*—Approximately 75 cm.
Stem:
*Length.*—Approximately 45 cm.
*Branching.*—Abundant.
*Pubescence.*—Present.
*Internode length.*—Approximately 1.8 cm.
*Color.*—Near R.H.S. 144B.
Leaf:
*Overall form.*—Long oblong.
*Apex form.*—Obtuse.
*Base form.*—Acute.
*Serrated, lobed or not.*—Serrated or lobed.
*Margin.*—Serrated or slightly lobed.
*Length.*—Approximately 3.5 cm.
*Width.*—Approximately 1.7 cm.
*Color of upper surface.*—Grayish olive green (R.H.S. 137A).
*Color of under surface.*—Moderate yellow green (R.H.S. 137C).
*Variegation.*—Absent.
*Leaf luster.*—Matte.
*Vein.*—Apparent.
*Leaf venation color.*—Near R.H.S. 144A.
*Petiole length.*—Approximately 2.5 cm.
*Leaf petiole diameter.*—Approximately 0.2 cm.
*Leaf petiole color.*—Near R.H.S. 143C.
*Stipule length.*—Approximately 1.5 cm.
*Stipule shape* (*type*).—Narrowly ovate pinnately parted.
*Stipule width.*—Approximately 0.6 to 0.8 cm.
*Stipule color.*—Upper side surface — Near R.H.S. 146B. Underside surface — Near R.H.S. 146C.
Flower:
*Bud.*—Shape — Lenticular. Length — Approximately 1.0–1.5 cm. Diameter — Approximately 0.2 to 0.4 cm. Color — Near R.H.S. 2B.
*Peduncle length.*—Approximately 10.0 cm.
*Peduncle diameter.*—Approximately 0.1 cm.
*Peduncle color.*—Strong yellow green (near R.H.S. 144A).
*Flower form.*—Vertically oblong.
*Flowering direction.*—Upward.
*Longitudinal diameter.*—Approximately 3.5 cm.
*Horizontal diameter.*—Approximately 2.6 cm.
*Flower depth.*—Approximately 0.9 cm.
*Ruffle of petal margin.*—Weakly ruffled.
*Petal curving.*—Weak.
*Number of petals per flower.*—Five (two upper petals, two side petals and one lower petal).
*Flower color.*—Single-colored.
*Upper petal.*—Size — Approximately 1.8×1.3 cm. Shape — Obovate. Apex shape — Rounded. Base shape — Truncate. Margin — Entire. Upper surface color — Near R.H.S. 5B, underside. Surface color — Near R.H.S. 3B. Blotch — Absent.
*Side petal.*—Size — Approximately 1.3×1.1 cm. Side petal shape — Obovate. Apex shape — Rounded. Base shape — Attenuate. Margin — Entire. Upper surface color — Near R.H.S. 5A; Underside. Surface color — Near R.H.S. 3B. Blotch — Absent.
*Lower petal.*—Size — Approximately 1.7×1.8 cm. Shape — Cordate. Apex shape — Emarginate. Base shape — Cuneate. Margin — Entire. Upper surface color — Near R.H.S. 5A; Underside. Surface color — Near R.H.S. 3B. Blotch — Absent. Eye color — Vivid yellow (Near R.H.S. 13A). Eye size — Small.
*Thickness of petal.*—Thin.
*Spur.*—Length — Approximately 0.6 to 0.8 cm. Diameter — Approximately 0.2 cm. Color — Near R.H.S. 157A.
*Sepal.*—Number — 5. Shape — Narrowly triangular. Length — Approximately 1.8 cm. Width — Approximately 0.3 cm. Upper surface color — Near R.H.S. 146C. Underside surface color — Near R.H.S. 145B.
*Number of flowers.*—Approximately 120 flowers present on a plant at one time.
*Pedicel.*—None.
Seed:
*Color.*—Deep brown, near R.H.S. 165B.
*Seed number.*—Approximately 10 per capsule.
*Seed shape.*—Ellipsoidal.
Physical property:
*Flowering time.*—From early November to June in Japan, except for Hokkaido.
*Time to produce.*—Approximately four months.
*Lastingness of an individual bloom on the plant.*—Approximately 5 to 7 days.
*Fragrance.*—Faint or weak.
*Resistance to rain.*—Medium.
*Winter hardiness.*—This variety has survived at a temperature of at least minus 7° C.
*Resistance to heat.*—Medium.
*Disease and pests.*— No serious damage by white fly, aphids, and bacterial disease has been observed.

This new variety of *Viola cornuta* plant 'Sunvioki' is most suitable for flower bedding and potting, hanging baskets and ground cover.

COMPARISON WITH SIMILAR VARIETY

The new variety of *Viola cornuta* plant 'Sunvioki' is different from a similar variety, 'Alpine Spring' in following points, 1. The plant width of 'Sunvioki' is wider than that of 'Alpine Spring'.
2. 'Sunvioki' has abundant branching compared to 'Alpine Spring' which has less branching.
3. The ruffle of petal margin of 'Sunvioki' is weakly ruffled while that of 'Alpine Spring' is flat.
4. 'Sunvioki' has single-colored flower while 'Alpine Spring' has multi-colored one.
5. The color of upper petal of 'Sunvioki' is R.H.S.5B while that of 'Alpine Spring' is R.H.S.2B.
6. The color of side petal of 'Sunvioki' is R.H.S.5A while that of 'Alpine Spring' is R.H.S.9B with R.H.S.79A vein.
7. The color of lower petal of 'Sunvioki' is R.H.S.5A while that of 'Alpine Spring' is R.H.S.9A vein.
8. The flowering time of 'Sunvioki' is early while that of 'Alpine Spring' is late.

The new variety of *Viola cornuta* plant 'Sunvioki' is different from a similar variety, 'Violetto Lune' in following points, 1. 'Sunvioki' has abundant branching compared to 'Violetto Lune' which has less branching.
2. The leaf color of upper surface of 'Sunvioki' is R.H.S.137A while that of 'Violetto Lune' is R.H.S.137B.
3. The color of upper petal of 'Sunvioki' is R.H.S.5B while that of 'Violetto Lune' is R.H.S.9A.
4. The color of side petal of 'Sunvioki' is R.H.S.5A while that of 'Violetto Lune' is R.H.S.9A.
5. The color of lower petal of 'Sunvioki' is R.H.S.5A while that of 'Violetto Lune' is R.H.S.12A.
6. The flowering time of 'Sunvioki' is early while that of 'Violetto Lune' is late.

It is claimed:

1. A new and distinct variety of *Viola cornuta* plant named 'Sunvioki', substantially as herein illustrated and described.

* * * * *